United States Patent [19]

Esposito et al.

[11] Patent Number: 6,030,530
[45] Date of Patent: Feb. 29, 2000

[54] NON-CYTOTOXIC POLYURETHANE MEDICAL ITEMS

[75] Inventors: Guy Esposito, Beynost, France; Pierre-Yves Herze, Ixeles, Belgium

[73] Assignee: Hospal Industrie, Meyzieu Cedex, France

[21] Appl. No.: 09/127,597

[22] Filed: Jul. 31, 1998

[30]     Foreign Application Priority Data

Jul. 31, 1997 [FR] France ................................ 97/10037

[51] Int. Cl.⁷ ......................... B01D 63/02; B01D 63/04; B01D 63/08; B01D 63/00; A61L 2/00
[52] U.S. Cl. ................................. 210/321.6; 210/321.61; 210/321.62; 210/321.71; 210/500.23; 210/500.24; 210/500.37; 422/28; 422/32; 525/452; 525/453; 528/49; 528/51; 528/72; 528/480; 528/483; 528/490; 528/491
[58] Field of Search ........................... 210/321.6, 321.61, 210/321.62, 321.71, 500.23, 500.24, 500.37; 422/28, 32; 525/452, 453; 528/49, 51, 72, 480, 483, 490, 491

[56] References Cited

U.S. PATENT DOCUMENTS

| | | | |
|---|---|---|---|
| 3,354,241 | 11/1967 | Larrison | 558/156 |
| 3,483,147 | 12/1969 | Friedman | 521/169 |
| 4,332,927 | 6/1982 | Simone | 528/58 |
| 4,621,113 | 11/1986 | Collins | 524/196 |
| 5,035,893 | 7/1991 | Shioya et al. | 424/447 |
| 5,306,798 | 4/1994 | Horn et al. | 528/58 |

FOREIGN PATENT DOCUMENTS

2147154   3/1973   France .

*Primary Examiner*—Rabon Sergent
*Attorney, Agent, or Firm*—Millen, White, Zelano & Branigan, P.C.

[57]     ABSTRACT

Medical article of manufacture comprising compositions, comprising: at least one polyisocyanate, preferably a non-aromatic polyisocyanate, in the monomer or prepolymer state; at least one polypol; and at least one organic compound comprising one or more phosphite functional groups, in the proportion of at least 1% by weight with respect to the total weight of the polyol or polyols, this organic compound being, in addition, non-aromatic and the carrier of at least one free hydroxyl group capable of reacting with an isocyanato group; and, if appropriate, at least one catalyst of the polymerization reaction of a polyisocyanate and of a polyol.

13 Claims, No Drawings

NON-CYTOTOXIC POLYURETHANE MEDICAL ITEMS

FIELD OF THE INVENTION

The subject-matter of the invention is medical items based on polyurethane-generating compositions which are non-cytotoxic after sterilization or disinfection by an oxidizing process and more particularly potting bodies for flat-membrane or hollow-fiber medical exchangers. Another subject-matter of the invention is a process for the preparation of these polyurethane medical items which makes it possible to greatly limit the cytotoxicity resulting from the sterilization or from the disinfection by an oxidizing process, such as ionizing radiation (gamma radiation, electron beam), gaseous peroxides (so-called cold plasma sterilization), liquid peroxides or any other physical or chemical process involving an oxidation reaction capable of denaturing the sterilized material.

Depending on the situation, the polyurethane potting bodies are intended to form:
  a cylindrical partition for separating the two compartments of a medical exchanger, the membrane of which is composed of a bundle of semi-permeable hollow fibers. The operation which consists in producing such a separating partition is usually denoted under the term "potting";
  or a leaktight seal in a medical exchanger comprising a semi-permeable flat membrane. The operation which consists in producing such a seal is usually denoted under the term "leaktightness packing". Nevertheless, in order to simplify the present description, this operation will also be denoted under the term "potting".

Out of concern for clarity of the present description, the term "seal" will be used to denote without distinction a leaktight seal in semi-permeable flat-membrane medical exchangers or a cylindrical separating partition in medical exchangers in which the membrane is composed of a bundle of semi-permeable hollow fibers.

The present invention is in particular of use in the manufacture of exchangers for medical applications in the form, for example, of dialysers, haemofilters and oxygenators.

BACKGROUND OF THE INVENTION

It is common practice to manufacture exchangers for medical applications by following the general stages which follow:
  preparing a semi-permeable membrane from a flat membrane or conforming a bundle of semi-permeable hollow fibers from hollow fibers;
  mounting the semi-permeable membrane or else the bundle of hollow fibers in a casing and forming, depending on the situation, a leaktight seal or a cylindrical partition for separating the two compartments, using a polyurethane-generating adhesive composition;
  if appropriate, attaching end fittings to the casing and sterilizing the medical device obtained.

The polyurethane-generating adhesive compositions used to prepare a seal in a medical exchanger generally comprise, before polymerization, one or more polyisocyanates, one or more polyols and, optionally, one or more polyfunctional crosslinking agents and/or one or more catalysts.

The polyurethane, once it is cured, has the essential function of forming a leaktight seal, in order for there to be no infiltration between the two compartments of the exchangers or with the outside. The risk of infiltration must in particular be avoided between the blood compartment and the dialysate compartment of medical exchangers for blood treatment. To achieve this, the polyurethane adhesive composition must exhibit satisfactory adhesion with the semi-permeable membranes of the exchangers, whatever the chemical nature of the materials of which they are composed. This composition must also exhibit satisfactory adhesion with the components of the exchangers with which it is brought into contact, such as the casing.

Another important quality required of exchangers for biomedical use is the biocompatibility of cured and sterilized polyurethane potting bodies, more especially their non-cytotoxicity. The stage of sterilization or of disinfection by an oxidizing process, in particular when it is a sterilization by irradiation, can render polyurethane cytotoxic.

Previously, in order to form non-cytotoxic potting bodies, various solutions were provided, thus:
  in U.S. Pat. No. 4,332,927, provision was made for polyurethane-generating compositions comprising at least one prepolymer with isocyanato endings (—NCO), at least one polyol and a catalytic amount of a dicarboxylated dialkyltin compound;
  in European Patents No. 0,393,545 and No. 0,413,265 and U.S. Pat. No. 5,306,798, various polyurethane-generating adhesive compositions based on diphenylmethane diisocyanates (MDI) or on MDI derivative, and on specific polyols, were provided.

SUMMARY OF THE INVENTION

It has now been discovered, differently and surprisingly, that it is possible to manufacture polyurethane medical items sterilized or disinfected by an oxidizing process which are non-cytotoxic, in particular polyurethane potting bodies, which are, in addition, sufficiently adhesive to semi-permeable membranes of exchangers but non-cytotoxic after sterilization or disinfection by an oxidizing process. In accordance with the invention, the starting point is a polyurethane-generating composition comprising:
  at least one polyisocyanate, preferably a non-aromatic polyisocyanate, in the monomer or prepolymer state;
  at least one polyol, in the monomer or prepolymer state;
  at least one organic compound comprising one or more phosphite functional groups, the amount of this organic compound being at least equal to 1% by weight with respect to the total weight of the polyol or polyols, this organic compound, in addition, being non-aromatic and the carrier of at least one free hydroxyl group (—OH) capable of reacting with an isocyanato group (—NCO); and
  advantageously, the polyurethane-generating composition additionally comprises at least one catalyst of the polymerization reaction of a polyisocyanate and of a polyol.

(Some polyurethane-generation generating compositions comprising a phosphite for flame and fire resistance are disclosed in U.S. Pat. Nos. 3,483,147 and 3,354,241.)

Another subject-matter of the present invention is a process which makes it possible to reduce the cytotoxicity of polyurethane medical items, in particular polyurethane potting bodies, liable to appear after sterilization or disinfection by an oxidizing process, characterized in that a polyurethane-generating composition is prepared from:
  at least one polyisocyanate, preferably a non-aromatic polyisocyanate, in the monomer or prepolymer state;
  at least one polyol;

at least one organic compound comprising one or more phosphite functional groups in an amount of at least 1% by weight with respect to the total weight of the polyol or polyols, this organic compound, being in addition, non-aromatic and the carrier of at least one free hydroxyl group (—OH) capable of reacting with an isocyanato group (—NCO); and if appropriate, at least one catalyst of the polymerization reaction of a polyisocyanate and of a polyol.

Thus, the organic compound comprising one or more phosphite functional groups can be bonded by chemical bonding in the polyurethane network. (Some polyurethane-generating compositions comprising a phosphite for flame and fire resistance are disclosed in U.S. Pat. Nos. 3,483,147 and 3,354,241.)

Still another aspect of the invention can be characterized as an improved article of manufacture comprising a potting compound in contact with a flat membrane or hollow fiber medical exchanger, wherein the improvement comprises the nature of the potting compound as described herein.

In the context of the present invention, the term non-cytotoxic polyurethane medical items is understood to mean items resulting in a percentage of inhibition of cell growth (% ICG) which is greatly reduced by virtue of the presence of at least one organic compound comprising one or more phosphite functional groups. This percentage of ICG is preferably at most equal to 30% on average over at least 3 samples, when the polyurethane medical items are subjected to the biological tests of medical and dental equipment and devices, part 5: in vitro methods, of the ISO Standard 10–993, supplemented by the conditions for measurement of cytotoxicity used by the Applicant Company. These specific conditions for measurement of cytotoxicity are set out hereinbelow, with the examples.

An essential characteristic of the invention lies in the use of at least one organic compound comprising one or more phosphite functional groups for preparing non-cytotoxic polyurethane medical items and more especially potting bodies for flat-membrane or hollow-fiber medical exchangers.

The general formula (I) of the organic compounds suitable for the invention and comprising at least one phosphite functional group is preferably the following:

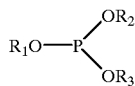

in which:

$R_1$, $R_2$ and $R_3$ are identical or different and represent an alkyl radical; $R_1$, $R_2$ and $R_3$ can be linear or branched, acyclic or cyclic; $R_1$, $R_2$ and $R_3$ are devoid of aromatic groups;

at least one radical $R_1$, $R_2$ or $R_3$ comprises at least one hydroxyl group (—OH);

In the above-mentioned general formula (I), only one phosphite functional group appears.

At least one radical $R_1$, $R_2$ or $R_3$ comprises advantageously one or more other phosphite functional groups according to the general formula (I).

In the continuation of the description, out of concern for simplification, the organic compounds (I) will be known as "phosphites (I)".

By virtue of the presence of at least one hydroxyl group, the phosphites (I) are advantageously hydrophilic. The hydroxyl group or groups of the phosphites (I) are preferably primary or secondary.

Phosphites (I) are advantageously chosen for which the melting point is less than or equal to 40° C. and, better still, which are liquid at room temperature, that is to say at a temperature of the order of 20–25° C.

Preferably, the phosphites (I) used comprise at least two phosphite functional groups, better still three phosphite functional groups.

The alkyl radicals $R_1$, $R_2$ or $R_3$ of the phosphites (I) can further comprise one or more heteroatoms, preferably one or more oxygen atoms in order to form one or more ether functional groups. Thus, the phosphites (I) can comprise one or more monovalent or divalent groups chosen from diethylene glycol, triethylene glycol, dipropylene glycol and dibutylene glycol.

Mention may be made, as examples of phosphites (I) suitable for the invention, of heptakis(dipropylene glycol) triphosphite (name abbreviated to PTP) and tris(dipropylene glycol) phosphite. The preferred phosphite (I) compound is PTP.

The amount of phosphite (I) to be provided in order to achieve satisfactory results in the cytotoxicity test (i.e., preferably at most 30% inhibition of cell growth on average over at least 3 samples) is at least equal to 1% by weight with respect to the total weight of the polyol or polyols. It is preferable for the amount of phosphite (I) not to exceed 10% by weight (with respect to the total weight of the polyols), in order to limit competition with the crosslinking polyol. The amount of phosphite (I) is preferably between 1.5% and 8% by weight with respect to the total weight of the polyol or polyols.

Use may be made, as examples of polyols capable of being suitable for the invention, of: castor oil; esters of polyol and of ricinoleic acid; polyether polyols, such as polyoxypropylene glycol and polytetramethylene ether glycols; homopolymers or copolymers of butadiene carrying at least two hydroxyl groups; esters of polyol and of fatty acid, such as soybean oil or castor oil, or esters of saturated or unsaturated diacid and of ethylene glycol, such as the adipate of poly(ethylene glycol); N,N,N',N'-tetrakis (hydroxypropyl)-ethylenediamine; polycaprolactone polyols; polyol oligomers, in particular polyol dimers which can comprise a cyclic and saturated hydrocarbon group and which are formed by condensation and complete reduction of two unsaturated fatty acids, or formed by condensation, partial reduction and esterification of two unsaturated fatty acids; prepolymer polyols obtained by reaction of an excess of polyols with a polyisocyanate, preferably a non-aromatic polyisocyanate; mixtures of two or more of the abovementioned polyols.

Mention may be made, as example of mixtures of polyols suitable for the invention, of:

a first mixture comprising:
  approximately 45% by weight of a polyol based on polyol esters and on polyether polyols, such as the product sold by Henkel under the name Sovermol 1080;
  approximately 25% by weight of castor oil;
  approximately 30% by weight of polycaprolactone polyol, such as a 50/50 mixture of the polyols sold by Solvay under the names Capa 305 and Capa 301.

a second mixture comprising:
  approximately 70% by weight of an ester of a diacidic dimer and ethylene glycol, such as the product sold by Unichema under the name Priplast 3193;
  approximately 15% of castor oil;
  approximately 15% of N,N,N',N'-tetrakis(2-hydroxypropyl)ethylenediamine.

The polyisocyanates which are suitable for the invention are preferably non-aromatic, that is to say devoid of one or more benzene, naphthalene or anthracene nuclei, and the like. Mention may be made, as examples of non-aromatic polyisocyanates, in the monomer or pre-polymer state, capable of being suitable for the invention, of aliphatic or cycloaliphatic polyisocyanates, such as dicyclohexylmethyl 4,4'-diisocyanate (HMDI), isophorone diisocyanate (IPDI), corresponding to 3-isocyanatomethyl-3,5,5-trimethylcyclohexyl isocyanate, trimethylhexamethylene diisocyanate, hexamethylene diisocyanate (HDI) and its condensation derivatives, such as HDI biuret and HDI isocyanurate. Aromatic polyisocyanates can also be used.

The amount of polyisocyanate reacted with the polyol should be sufficient to provide at least one isocyanato group per polyol hydroxyl group. An NCO/OH ratio by number equal to or greater than 1, preferably equal to or greater than 1.1, is advantageous.

Of course, the polyurethane compositions according to the invention can comprise various additives conventionally used in the technical field involved, such as:

- at least one catalyst for accelerating the crosslinking, preferably in the proportion of 0.01 to 2% by weight of the overall composition. Mention may be made, as example of catalyst suitable for the present invention, of tin carboxylates, such as dibutyltin dilaurate (DBTL). The presence of a catalyst is recommended when the polyisocyanates are non-aromatic;
- at least one adhesion promoter for conferring, on the cured polyurethane, improved adhesion to the semi-permeable flat membranes or hollow fibers, in particular when the medical exchanger is composed of a negatively charged semi-permeable membrane [i.e. a membrane comprising negative charges in excess which can be detected, in particular by flow measurements (Zeta potential)]. A PEI (polyethylemeimine) with a weight-average molecular mass ranging from approximately 600 to approximately 10,000, easier to process due to their lower viscosity at ambient temperature, is preferably chosen. The PEI can be processed according to two different processes (a) or (b) which follow:
  a) the PEI can be used to treat the outer surface of the semi-permeable membranes. It is then applied to the outer surface of the fibers or of the channels formed by the flat semi-permeable membranes;
  b) the PEI can be incorporated in the polyurethane-generating adhesive composition. It is then mixed with one or more of the components which are used to prepare a polyurethane-generating adhesive composition.

A patent representative of the technique of the use of PEI as adhesion promoter for potting bodies is European Patent Application No. 0,710,683.

Various processes can be used for the preparation of the polyurethane medical items according to the invention.

In accordance with a preferred embodiment, a polyurethane-generating composition is prepared from two components which are stored separately, respectively a first component composed of at least one polyisocyanate in the monomer or prepolymer state and a second component composed of at least one polyol and of at least one non-aromatic phosphite (I) carrying at least one free OH group, in the proportion of at least 1% by weight of phosphite (I) with respect to the weight of the polyol or polyols, and, if appropriate, of at least one catalyst and/or of at least one adhesion promoter. These two components are mixed, until a homogeneous mixture is obtained, at the time of the manufacture of the medical item, such as a leaktight polyurethane seal.

The polyurethane-generating composition can also be presented, before use, as three components, respectively a first component composed of at least one polyisocyanate, in the monomer or prepolymer state, a second component composed of at least one polyol and, optionally, of at least one catalyst and/or at least one adhesion promoter, and a third component composed of at least one non-aromatic phosphite (I) compound carrying at least one free OH group, in the proportion of at least 1% by weight of phosphite (I) with respect to the weight of the polyol or polyols.

The polyurethane-generating adhesive compositions according to the invention are particularly well suited to negatively charged semi-permeable membranes and are conformed into a single type of material which comprises in particular an acrylonitrile homo- or copolymer in the form of a flat membrane or of a bundle of hollow fibers.

Such a material, when it is composed of one or more acrylonitrile copolymers, can comprise:

(1) a copolymer of acrylonitrile and of at least one anionic or anionizable monomer comprising, if appropriate, units originating from at least one other monomer containing olefinic unsaturation capable of being copolymerized with the acrylonitrile, or (2) a copolymer of acrylonitrile and of at least one anionic or anionizable monomer and of at least one non-ionic and non-ionizable monomer.

Some of these macromolecular compounds, and the various monomers capable of being used as starting materials in their manufacture, are more fully disclosed in U.S. Pat. No. 4,545,910, regranted under Re. No. 34239.

Among these macromolecular compounds, those with which the polyurethane-generating adhesive compositions according to the invention are particularly well suited are defined under (1) above, in particular when the semi-permeable membrane is in the hydrogel state. In particular, the invention is particularly well suited to those in which the anionic or anionizable comonomer is olefinically unsaturated and carries anionic groups chosen from sulphonate, carboxyl, phosphate, phosphonate and sulphate groups and more particularly still when this comonomer is sodium methallylsulphonate.

Of course, the precise nature of the counterion of the anionic groups is not essential to the satisfactory operation of the invention.

Mention may be made, among monomers containing olefinic unsaturation capable of being copolymerized with acrylonitrile, of alkyl acrylates and, in particular, methyl acrylate.

The examples below illustrate the invention without in any way limiting the scope thereof.

EXAMPLES

Preparation of a polyurethane (PUR) from an adhesive composition, in two components, incorporating or not incorporating a phosphite compound A specific amount of polyol is introduced into a vessel equipped with a stirrer. A specific amount of polyethyleneimine (PEI) with an average molecular mass of the order of 600 is weighed out and this amount is introduced into the vessel. If appropriate, a specific amount of phosphite (I) is weighed out and this amount is introduced in its turn into the vessel. Stirring is then carried out, under a nitrogen or dry air atmosphere, until the mixture is homogenized. The mixture is subsequently degassed under vacuum, at ambient temperature or under warm conditions (maximum 40° C.), before it is used in the preparation of the polyurethane by mixing with a polyisocyanate, itself degassed under vacuum (to avoid the presence of bubbles).

The level of catalyst is adjusted according to the pot life desired.

For approximately half of its composition (first component), the PUR is obtained from a so-called isocyanate part. The other part of the composition used to prepare the PUR (second component) comprises the stable mixture of polyol, of PEI, of above-mentioned catalyst and, if appropriate, of phosphite (I). The proportions of the isocyanate part and of the polyol part are calculated as a function of the equivalent weight of isocyanato group (NCO) and of the equivalent weight of hydroxyl group (OH), in order to have an NCO/OH ratio equal to 1.1.

For Examples 1a, 1b, 2a and 2b, the chemical nature and the amount of the polyols, of the phosphite (I), of the polyisocyanate and of the catalyst appear in the table below.

Potting of the hollow fibers

The potting with a polyurethane (PUR) -generating adhesive composition requires a prior drying, at least, of the ends of the bundle of fibers which will be in contact with the PUR.

The polyurethane-generating adhesive composition is subsequently prepared by mixing the first and second components mentioned in the preceding paragraph for the requirements of the examples.

Immediately afterwards, the composition is poured into a tank equipped with small tubes connected to the two ends of a tubular casing where a bundle of hollow fibers has been introduced and where it has to be potted at its two ends. Prior to this operation, the casing has been equipped with stoppers at its ends in order to contain the adhesive during the potting proper.

The casing comprising the bundle of fibers is rotated about an axis which is perpendicular to the longitudinal axis of the bundle and which passes through the mid-length of the device. Under the effect of the centrifigal force, the composition is displaced to the ends of the bundle of fibers and coats these. The composition also penetrates inside the fibers but this penetration is limited by the compression of the air

| Chemical nature of the components | Example 1a | Example 1b | Example 2a | Example 2b |
|---|---|---|---|---|
| | Amount of each component (as % by weight) | | | |
| Isocyanate component based on hexamethylene diisocyanate (HDI) | 48.7 | 48.7 | 0 | 0 |
| Polyol component based on (% by weight): 45% of a product comprising polyol esters and polyether polyols sold under the name Sovermol 1080 by Henkel (OH value in mg KOH/g of product = 170) 25% of castor oil 15% of polycaprolatone polyol sold under the name Capa 305 by Solvay (molecular weight 540; OH value in mg KOH/g of product 310) 15% of polycaprolactone polyol sold under the name Capa 301 by Solvay (moecular weight = 300; OH value in mg KOH/g of product = 560) 0.1% (*) of PEI 0.15% (*) of dibutyltin dilaurate (DBTL) | 51.3 | 51.3 | 0 | 0 |
| Isocyanate component based on HDI isocyanurate (sold by Bayer under the name Desmodur W) | 0 | 0 | 36.3 | 36.3 |
| Polyol component based on (% by weight): 70% of an ethylene glycol dimerate (1) with a moecular weight equal to 1000 sold by Unichema under the name Priplast 3193 (OH value in mg KOH/g of product = 106) 15% of castor oil 15% of N,N,N',N'-tetrakis(2-hydroxypropyl)ethylenediamine 0.15% (*) of PEI 0.5% (*) of DBTL | 0 | 0 | 63.7 | 63.7 |
| Phosphite (I) compound added to the polyol component Heptakis(dipropylene glycol) triphosphite | 0 | 3(*) | 0 | 5(*) |

(*) Additional percentage with respect to the polyol mass.
(1) The ethylene glycol dimerate is obtained by reaction (esterification) of diacidic dimer and ethylene glycol. The diacidic dimer results from the esterification of a C-36 (36 carbon atoms) diol dimer and of diacids.

trapped within the fibers. In addition, this penetration is controlled by varying two parameters: the centrifugal force (i.e. the rotational speed of the device) and the air temperature.

After polymerizing the composition, the stoppers are removed and the potting body is cut at a level beyond the penetration of the composition in the fibers, so that the fibers are open in order to allow circulation of fluid inside the fibers.

Once assembling is completed, the product obtained is hermetically packed in a bag in order to be protected from any microbiological contamination after sterilization.

The sterilization method chosen is gamma irradiation at an irradiation dose at least equal to 25 kGy, guaranteeing a negligible probability of microbiological contamination after sterilization.

Protocol for measuring the cytotoxicity of a polyurethane (PUR)

In the examples, the cytotoxicity of the cured polyurethane (PUR) adhesive compositions was measured in accordance with the recommendations of ISO Standard 10–993, part 5, supplemented in the following way by the company Hospal:

On D1 (1st day), under aseptic conditions, a mouse fibroblast cell line (L929) is inoculated at low density at the bottom of culture wells (5000 cells per 0.32 $cm^2$ well). The cells, cultured in a culture medium to which has been added 10% of foetal calf serum (comprising growth factors), adhere to the plastic before dividing.

On D2 (2nd day), at the time when the cells enter into logarithmic growth phase, the cells are brought into contact with the aqueous eluate of the PUR studied, which is liable to comprise extractable substances.

The conditions for the preparation of the aqueous eluate of the PUR studied, in particular the surface area/volume and temperature/duration ratios, are described in ISO Standard 10–993, part 12.

The aqueous eluate of the PUR is diluted to half with a 2X (two times concentrated) culture medium. A dilution of the eluate to ¼ was also tested after dilution to half in a 1X culture medium of the preceding solution.

On D5 (5th day), the culture wells are emptied, the cellular layer is washed and the density and the viability of the cells are quantified using a standardized solution of a vital stain (neutral red) captured by living cells.

Approximately 3 hours later, the excess stain is removed by washing and the captured stain is extracted with a predetermined volume of a solution of acetic acid and of ethanol.

The cytotoxicity is determined with respect to an absolute growth control, where the 2x culture medium was diluted to half with water for injectable preparation (i.e. demineralized and doubly-distilled water), in which the cells are left for 5 days to become subconfluent, that is to say high density.

A positive control is systematically carried out using a toxic reference substance ($HgCl_2$, and the like). The preparation of the positive control involves diluting a 2x culture medium to half with water for injectable preparation, adding 6 µg/ml of $HgCl_2$ and leaving the cells for 5 days in this dilute toxic medium.

The relative cytotoxicity for each eluate is expressed, by difference with the absolute growth control, as percentage of inhibition of cell growth (% ICG).

The coloration of the solution of acetic acid and of ethanol depends on the concentration of living cells and is measured using a plate reader in the UV/visible, according to the following procedure:

ICG (%)=100(D−d)/D, where

D represents the optical density of the absolute growth control, d represents the optical density of the sample.

In addition, the results reported in the table below correspond to the average of three tested samples.

The results of the cytotoxicity measurements on the PURs of Examples 1a, 1b, 2a and 2b are reported in the table below.

| EXAMPLE No. | % ICG of the eluate (37° C./48 h - 12 $cm^2$/1 ml) | |
|---|---|---|
| | Eluate diluted to ½ | Eluate diluted to ¼ |
| 1a | 67 | 8 |
| 1b | 26 | 10 |
| 2a | 78 | 36 |
| 2b | 25 | 9 |

In the light of these results, it is clearly apparent that the PUR formulations of Examples 1b and 2b, including the phosphite compound PTP, result in the lowest values of inhibition of cell growth (% ICG). In accordance with the invention, the PURs of Examples 1b and 2b are considered non-cytotoxic.

The preceding examples can be repeated with similar success by substituting the generically or specifically described reactants and/or operating conditions of this invention for those used in the preceding examples.

The entire disclosure of all applications, patent and publications, cited above, and of corresponding French Appln. No. 97/10037, filed Jul. 3, 1997, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an article of manufacture comprising a polyurethane potting body in contact with a flat-membrane or hollow-fiber medical exchanger, the improvement wherein the potting body is obtained from polyurethane-generating compositions comprising:

at least one polyisocyanate, in the monomer or prepolymer state;

at least one polyol;

at least one organic compound comprising one or more phosphite functional groups, in the proportion of at least 1% by weight with respect to the total weight of the polyol or polyols, said organic compound being non-aromatic and having at least one free hydroxyl group capable of reacting with an isocyanato group; and optionally, at least one catalyst of the polymerization reaction of a polyisocyanate and of a polyol.

2. An article of manufacture according to claim 1, wherein the organic compound comprising at least one phosphite functional group has the general formula (I):

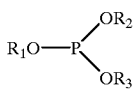

in which:
- $R_1$, $R_2$ and $R_3$ are identical or different and represent a linear or branched, acyclic or cyclic alkyl radical but are devoid of aromatic groups;
- at least one radical $R_1$, $R_2$ or $R_3$ comprises at least one hydroxyl group (—OH).

3. An article of manufacture according to claim 2, wherein the hydroxyl group or groups present in the radical or radicals $R_1$, $R_2$ and $R_3$ are primary or secondary.

4. An article of manufacture according to claim 2, wherein at least one radical $R_1$, $R_2$ or $R_3$ comprises one or more phosphite functional groups.

5. An article of manufacture according to claim 2, wherein the melting point of the organic compound is less than or equal to 40° C.

6. An article of manufacture according to claim 5, wherein the organic compound is liquid at room temperature.

7. An article of manufacture according to claim 6, wherein the organic compound is chosen from the group consisting of heptakis(dipropylene glycol) triphosphite and tris(dipropylene glycol) phosphite.

8. An article of manufacture according to claim 1, wherein the amount of organic compound does not exceed 10% by weight with respect to the total weight of the polyol or polyols.

9. An article of manufacture according to claim 8, wherein the amount of organic compound is between 1.5 and 8% by weight with respect to the total weight of the polyols.

10. An article of manufacture according to claim 1, wherein said at least one polyisocyanate is a non-aromatic polyisocyanate.

11. An article of manufacture defined in claim 1, wherein the at least one polyol is composed of the following combination:
- approximately 45% by weight of a polyol wherein said polyol is other than caster oil or polycaprolactone polyol, and is at least one of a polyol ester and a polyether polyol;
- approximately 25% of castor oil; and
- approximately 30% of polycaprolactone polyol.

12. An article of manufacture defined in claim 1, wherein the at least one polyol is composed of the following combination:
- approximately 70% by weight of an ester of a diacidic dimer and ethylene glycol;
- approximately 15% of castor oil; and
- approximately 15% of N,N,N',N'-tetrakis(2-hydroxypropyl)ethylenediamine.

13. A process for reducing the cytotoxicity of polyurethane medical articles after sterilization or disinfection by an oxidizing process, comprising providing a polyurethane-generating composition prepared from at least one polyisocyanate, in the monomer or prepolymer state, from at least one polyol, from at least one organic compound comprising one or more phosphite functional groups, in the proportion of at least 1% by weight with respect to the total weight of the polyol or polyols, said organic compound being, in addition, non-aromatic and having at least one free hydroxyl group capable of reacting with an isocyanato group, and, optionally, from at least one catalyst of the polymerization reaction of a polyisocyanate and of a polyol, as a component of said medical article, and sterilizing or disinfecting by an oxidation process said article.

* * * * *